United States Patent
Borden

(10) Patent No.: US 11,783,244 B2
(45) Date of Patent: Oct. 10, 2023

(54) METHODS AND SYSTEMS FOR HOLISTIC MEDICAL STUDENT AND MEDICAL RESIDENCY MATCHING

(71) Applicant: Jonathan Harris Borden, South Burlington, VT (US)

(72) Inventor: Jonathan Harris Borden, South Burlington, VT (US)

(73) Assignee: Jonathan Harris Borden, South Burlington, VT (US)

( * ) Notice: Subject to any disclaimer, the term of this patent is extended or adjusted under 35 U.S.C. 154(b) by 0 days.

(21) Appl. No.: 17/840,192

(22) Filed: Jun. 14, 2022

(65) Prior Publication Data

US 2022/0399106 A1   Dec. 15, 2022

Related U.S. Application Data

(60) Provisional application No. 63/245,031, filed on Sep. 16, 2021, provisional application No. 63/210,380, filed on Jun. 14, 2021.

(51) Int. Cl.
  *G06Q 10/0631*   (2023.01)
  *G16H 40/20*     (2018.01)
  *G06F 16/335*    (2019.01)

(52) U.S. Cl.
  CPC ..... *G06Q 10/063112* (2013.01); *G16H 40/20* (2018.01); *G06F 16/335* (2019.01)

(58) Field of Classification Search
  CPC .................. G16H 40/20; G06F 16/335; G06Q 10/063112
  USPC ...................................................... 705/7.14
  See application file for complete search history.

(56) References Cited

U.S. PATENT DOCUMENTS

| | | | |
|---|---|---|---|
| 11,393,061 B2 * | 7/2022 | Al-Sulaiman | G06Q 50/2053 |
| 2014/0052663 A1 | 2/2014 | Kelley et al. | |
| 2014/0279620 A1 | 9/2014 | Lillquist et al. | |
| 2015/0095083 A1 | 4/2015 | Signer et al. | |
| 2015/0310456 A1 * | 10/2015 | Vandenburgh | G06Q 30/0201 |
| | | | 705/7.32 |
| 2016/0275803 A1 * | 9/2016 | Martin | G09B 5/06 |
| 2016/0371279 A1 * | 12/2016 | Bai | G06Q 50/01 |
| 2017/0323408 A1 | 11/2017 | Wager et al. | |
| 2017/0358230 A1 * | 12/2017 | Martin | G09B 5/06 |
| 2018/0293679 A1 * | 10/2018 | Bai | G06Q 50/01 |

(Continued)

OTHER PUBLICATIONS

Fernandez, et al., Evaluation of a Medical Student Research and Career Development Program to Increase Diversity in Academic Medicine, 94 Academic Medicine 8, pp. 1220-1228 (2019) (Year: 2019).*

(Continued)

*Primary Examiner* — Charles Guiliano
(74) *Attorney, Agent, or Firm* — CALDWELL INTELLECTUAL PROPERTY LAW

(57) ABSTRACT

A method for holistically ranking medical student and medical residency matching including, generating an applicant profile, determining a diversity score as a function of data in the applicant profile, determining a competency score as a function of data in the applicant profile, and calculating a representative score as a function of the diversity score and the competency score. Further, the method includes presenting, via a graphical user interface (GUI) a graphical representation of the representative score.

16 Claims, 7 Drawing Sheets

(56) References Cited

U.S. PATENT DOCUMENTS

2019/0102854 A1   4/2019  Terra et al.
2020/0294166 A1   9/2020  Vos et al.
2020/0302296 A1*  9/2020  Miller ..................... G06N 5/01

OTHER PUBLICATIONS

McLaughlin, et al., Using Composite Metrics to Measure Student Diversity in Higher Education, 37 Journal of Higher Education Policy and Management 2, pp. 222-224 (2015) (Year: 2015).*
Jeremy R. Rinard, Ben D. Garol, Ashvin B. Shenoy, Raman C. Mahabir, Successfully matching into surgical specialties: an analysis of national resident matching program data, Sep. 30, 2010.

* cited by examiner

METHODS AND SYSTEMS FOR HOLISTIC MEDICAL STUDENT AND MEDICAL RESIDENCY MATCHING

CROSS-REFERENCE TO RELATED APPLICATIONS

This application claims the benefit of priority of U.S. Provisional Patent Application Ser. No. 63/210,380, filed on Jun. 14, 2021, and titled "METHODS AND SYSTEMS FOR ENHANCED DIVERSITY AND OPPORTUNITY WITHIN THE MEDICAL RESIDENT SELECTION PROCESS," and further claims the benefit of priority of U.S. Provisional Application Ser. No. 63/245,031, filed on Sep. 16, 2021, and titled "METHODS AND SYSTEMS FOR RANKING APPLICANTS BASED ON DIVERSITY AND COMPETENCY SCORES" which are both incorporated by reference herein in their entirety.

FIELD OF THE INVENTION

The present invention generally relates to the field of computer science. In particular, the present invention is directed to methods and systems for holistically matching medical students and medical residencies based on diversity and competency scores.

BACKGROUND

Currently, the medical residency selection process relies mainly on academic factors such as an applicant's United States Medical Licensing Exam scores and the number of publications by that applicant to assess an applicant's future potential in that field. As a result, many applicants that would otherwise be great potential matches to the respective program but come from medical schools without the intrinsic opportunities and resources necessary to be a competitive applicant are turned down in favor of applicants that come from medical schools with the intrinsic opportunities and resources necessary to support the academic efforts to be a competitive applicant such as the number of publications and extracurricular projects available.

SUMMARY OF THE DISCLOSURE

In an aspect, a method for holistic medical student and medical residency matching including: generating, by a processor, an applicant profile, wherein generating the applicant profile includes receiving, by the processor, applicant data, generating, by the processor, a textual query for the applicant data, applying, by the processor, the textual query to the applicant data, extracting, by the processor, a textual output based at least on the textual query, and producing, by the processor, the applicant profile based at least on the textual output of the textual query. Also, the method includes: determining, by the processor, a diversity score, wherein determining the diversity score includes parsing the applicant profile for diversity data associated with predetermined diversity indices, extracting the diversity data associated with predetermined diversity indices, converting the diversity data associated with predetermined diversity indices into numerical diversity values, and calculating, based at least on the numerical diversity values, the diversity score. Further, the method includes: determining, by the processor, a competency score, wherein determining the competency score includes: parsing the applicant profile for competency data associated with predetermined competency indices, extracting the competency data associated with predetermined competency indices, converting the competency data associated with predetermined competency indices into numerical competency values, and calculating, based at least on the numerical competency values, the competency score. Moreover, the method may include calculating, by the processor, a representative score for an applicant based at least on the applicant diversity score and the applicant competency score; and presenting, on a graphical user interface (GUI), a graphical representation of the representative score.

In another aspect, a system for holistic medical student and medical residency matching including: generating, by a processor, an applicant profile, wherein generating the applicant profile includes receiving, by the processor, applicant data, generating, by the processor, a textual query for the applicant data, applying, by the processor, the textual query to the applicant data, extracting, by the processor, a textual output based at least on the textual query, and producing, by the processor, the applicant profile based at least on the textual output of the textual query. Also, the system includes: determining, by the processor, a diversity score, wherein determining the diversity score includes parsing the applicant profile for diversity data associated with predetermined diversity indices, extracting the diversity data associated with predetermined diversity indices, converting the diversity data associated with predetermined diversity indices into numerical diversity values, and calculating, based at least on the numerical diversity values, the diversity score. Further, the system includes: determining, by the processor, a competency score, wherein determining the competency score includes: parsing the applicant profile for competency data associated with predetermined competency indices, extracting the competency data associated with predetermined competency indices, converting the competency data associated with predetermined competency indices into numerical competency values, and calculating, based at least on the numerical competency values, the competency score. Moreover, the system includes calculating, by the processor, a representative score for an applicant based at least on the applicant diversity score and the applicant competency score; and presenting, on a graphical user interface (GUI), a graphical representation of the representative score.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for methods and systems for enhanced diversity and opportunity within the medical resident selection process. In an embodiment, the system may generate a ranking score of an applicant based on a diversity and competency scores of the applicant, where the data used to generate the scores are produced data input from a plurality of sources.

Aspects of the present disclosure can be used to improve the residency selection process by utilizing a competency-based approach to automatically evaluate and stratify applicants per application while maximizing diversity, in view of predicted performance, where the diversity may be based on inherent or acquired attributes. Maximum predicted performance of a cohort may not require maximum diversity or maximum competency, aspects of the present disclosure describe as much. Aspects of the present disclosure can also be used to apply a competency-based approach that maximizes diversity to a plurality of academic programs, such as a Law School admittance process. This is so, at least in part, because the system's ranking score based on competency and diversity scores can be applied to a plurality of fields of practice.

Aspects of the present disclosure allow for producing an applicant profile from a plurality of data sources, including, but not limited to data in natural language format such as a personal statement or recommendation letter, and/or quantitative data such as test scores, grade point averages, and the like thereof. Exemplary embodiments illustrating aspects of the present disclosure are described below in the context of several specific examples.

Figure 1:
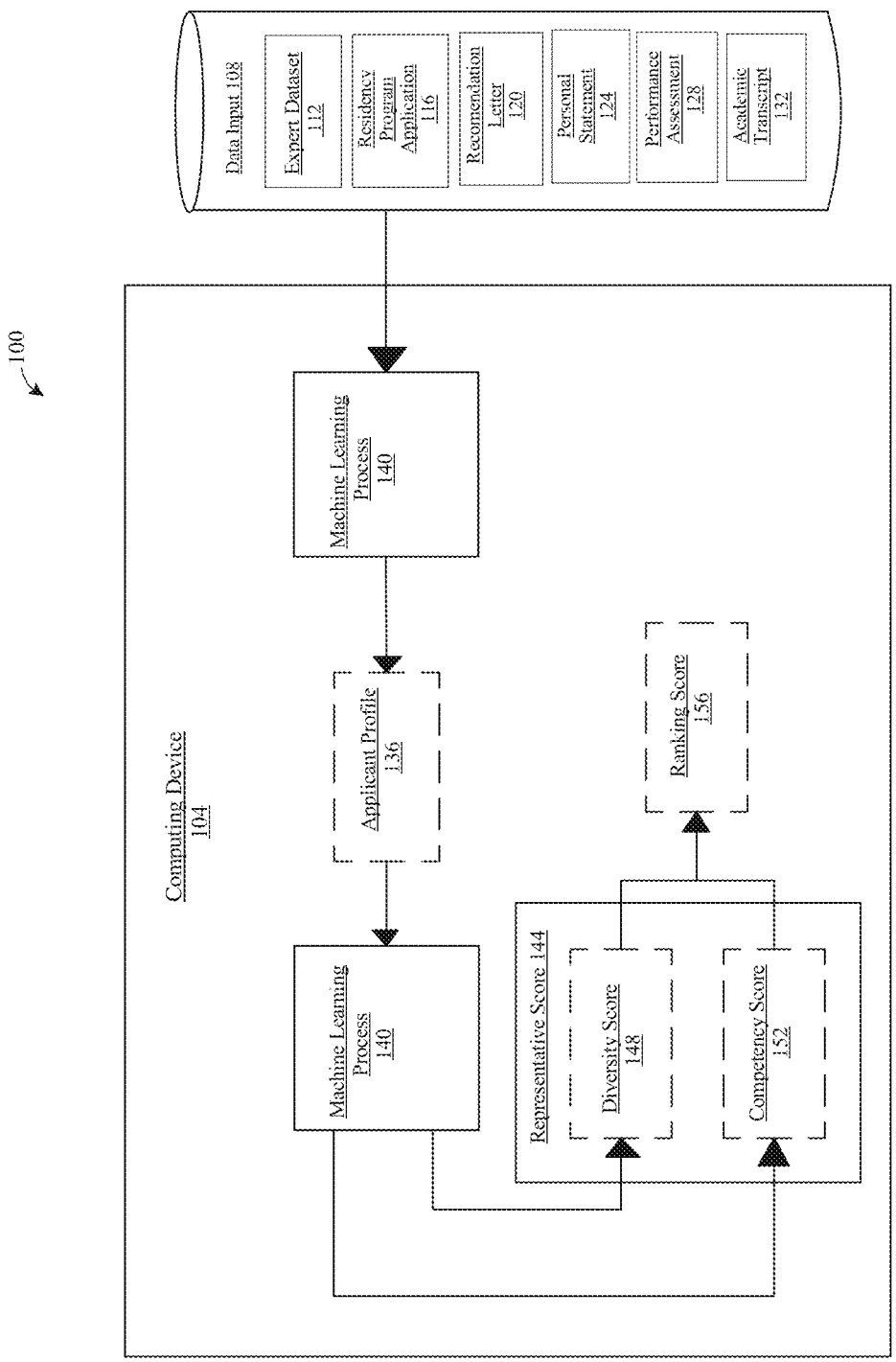
FIG. 1 is a block diagram illustrating a system of diverse candidate selection.

Referring now to FIG. 1, an exemplary embodiment of a system 100 for enhanced diversity and opportunity within the medical resident selection process is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 is configured to receive a data input 108. In an embodiment, data input 108 may be received from a remote device. In another embodiment, data input 108 may be received from an expert dataset 112, such as, but not limited to, datasets received from one or more organizations comprising Association from American Medical Colleges (AAMC), American Osteopathic Association, American Association of Colleges of Osteopathic Medicine, a university, research institution, hospital and the like thereof. In a nonlimiting example, data input 108 may be received directly from the AAMC through an API endpoint. Data input 108 may include a plurality of data such as general applicant data, an expert dataset 112, a residency program application 116, a recommendation letter 120, a personal statement 124, a performance assessment 128, academic transcript 132 and the like.

Continuing to refer to FIG. 1, computing device 104 is configured to produce an applicant profile 136 as a function of the data input 108. An "applicant profile" is a representative set of documents and/or data for an applicant. In some instances, an applicant profile 136 may include an expert dataset 112, a residency program application 116, a recommendation letter 120, a personal statement 124, a performance assessment 128, academic transcript 132 and the like. Additionally, an applicant profile 136 may include an applicant identifier that may be used as a reference for the applicant profile 136. In one embodiment, data input 108 may be an unstructured dataset. In one embodiment, data input 108 may be a structured dataset. In another embodiment, data input 108 may include data in natural language format such as recommendation letters, performance assessments, personal statement, and the like. In one embodiment, data input 108 may be received from any publicly available website. In a nonlimiting example, data input 108 may be an applicant's application to the residency program.

Still referring to FIG. 1, producing the applicant profile 136 includes determining an applicant identifier as a function of the data input 108, generating at least a query as a function of the application identifier, extracting at least a textual output as a function of the at least a query, and producing the applicant profile 136 as a function of the at least a textual output.

Alternatively, or additionally, producing the applicant profile 136 may further include utilizing a machine learning process 140. In one embodiment, producing the applicant profile 136 may further include utilizing a language processing module. Language processing module may include any hardware and/or software module. Language processing module may be configured to extract, from the one or more documents, one or more words. One or more words may include, without limitation, strings of one or more characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Language processing module may operate to produce a language processing model. Language processing model may include a program automatically generated by computing device and/or language processing module to produce associations between one or more words extracted from at least a document and detect associations, including without limitation mathematical associations, between such words. Associations between language elements, where language elements include for purposes herein extracted words, relationships of such categories to other such term may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of semantic meaning. As a further example, statistical correlations and/or mathematical associations may include probabilistic formulas or relationships indicating a positive and/or negative association between at least an extracted word and/or a given semantic meaning; positive or negative indication may include an indication that a given document is or is not indicating a category semantic meaning. Whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at computing device, or the like.

Further, language processing module and/or diagnostic engine may generate the language processing model by any suitable method, including without limitation a natural language processing classification algorithm; language processing model may include a natural language process classification model that enumerates and/or derives statistical relationships between input terms and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between extracted words, phrases, and/or other semantic units. There may be a finite number of categories to which an extracted word may pertain; an HMM inference algorithm, such as the forward-backward algorithm or the Viterbi algorithm, may be used to estimate the most likely discrete state given a word or sequence of words. Language processing module may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

In some embodiments, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Further, language processing module may use a corpus of documents to generate associations between language elements in a language processing module, and diagnostic engine may then use such associations to analyze words extracted from one or more documents and determine that the one or more documents indicate significance of a category. In an embodiment, language module and/or computing device may perform this analysis using a selected set of significant documents, such as documents identified by one or more experts as representing good information; experts may identify or enter such documents via graphical user interface, or may communicate identities of significant documents according to any other suitable method of electronic communication, or by providing such identity to other persons who may enter such identifications into computing device. Documents may be entered into a computing device by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, diagnostic engine may automatically obtain the document using such an identifier, for instance by submitting a request to a database or compendium of documents such as JSTOR as provided by Ithaka Harbors, Inc. of New York. In some embodiments, computing device may extract data of interest from raw portable document format (PDF) and/or excel format and transform the data of interest into an analyzable format.

In some embodiments, producing the applicant profile 136 may further include a deep learning algorithm. In one embodiment, producing the applicant profile 136 may include utilizing an Artificial Neural Network. In one embodiment, the machine learning process 140 may be trained with data from a plurality of sources including data input, publicly available websites, resident applications, AAMC, open sources, web scraping, remote databases, and the like. For instance and without limitation, machine learning process 140 may be trained from one or more open sources of data such as but not limited to data available from World Health Organization (WHO), Center for Disease Control and Prevention (CDC), Data.gov, Re3Data, Child Health and Development Studies (CHDS), Kent Ridge Biomedical Datasets, Merck Molecular Health Activity Challenge, Surveillance, Epidemiology, and End Results Program (SEER), 1000 Genomes Project, Medicare, Medicaid, Healthcare Cost and Utilization Project (HCUP), Deep Lesion, CT Medical Images, Kaggle, Subreddit, Healthcare.ai and the like. A Machine learning module and neural network are described in detail further below.

Continuing to refer to FIG. 1, computing device 104 is further configured calculate a representative score 144 as a function of the applicant profile 136. As used in this disclosure a "representative score" is a measurable value denoting one or more characteristics and/or qualities associated to an applicant. In an embodiment, and without limitation, computing device 104 may be configured to utilize machine learning processes 140 to calculate representative score 144. In one embodiment, calculating representative score 144 may further include utilizing an artificial neural network. In one embodiment, calculating representative score 144 may include utilizing inherent and acquired attributes of an applicant. As a non-limiting example, representative score 144 may include a diversity score 148. A "diversity score" is a measure, metric, or other quantitative value representing a degree of difference, in a plurality of demographic categories, from a given population. A diversity score 148 may represent inherent diversity attributes. In some instances, a diversity score 148 may represent attributes that an applicant is born with and/or acquired throughout life experiences. For example, a diversity score may be a value between 0 and 1 for a demographic category. A demographic category may be associated with predetermined diversity indices, as described herein. As such, for a demographic category like "race", an applicant may be assigned a score between 0 and 1. Regarding a score between 0 and 1, a score closer to 0 may imply less diversity than a score closer to 0. It should be noted that a score being between 0 and 1 implies a scale and that the score is not meant to be interpreted as binary code inputs (i.e., 0, 1). That is, the scores may represent homogeneity in a given population such that a value of 0 represent a fully homogenous given population while a value of 1 represents a given population where each individual is different with regard to a particular demographic category. It should be noted that a diversity score value may have at least 2 significant digits but may have more. In an embodiment, calculating the diversity score 148 may include using a Sullivan's Composite Diversity Index where the diversity of a given population represents the relative proportion of categories present across all diversity attributes, which may be expressed by the following formula:

$$A_w = 1 - \sum_{i=1}^{k} \left[ \frac{(p_i)^2}{V} \right]$$

Where there are V attributes, k categories and $p_i$ proportions in each category. $A_w$ is interpreted as the probability that any two individuals, from a given population, drawn at random will be from different categories across all diversity attributes. $A_w$, within a given population, is maximized with increasingly equal representation among many categories across multiple attributes. In some instances, a given population may be the population of the entity or institution that an applicant is applying to. Also, a given population maybe a population of likely patients that an applicant may need to interact with upon admission to a residency program. Further, a given population may be dependent on a geographical area in which applicant may serve upon admission to a residency program. Moreover, a given population may be any combination of the given populations described herein. It should be noted that a diversity score may be computed for each given population as described above. As such, the respective diversity scores may then be aggregated, averaged. or any mathematical computation seen fit. In some instances, aggregation may include inputting given population data into a machine learning model. In yet another non-limiting example, calculating diversity score 148 may be performed utilizing a Shannon Weiner index and/or a multidimensional diversity index.

In some embodiments, a computing device 104 may identify populations using a predictive model that may be generated via a machine learning model. A machine learning model for generating a predictive model may be produced as described herein. Inputs maybe description of known diversity data for people within a geographical area and outputs may be estimated diversity data and/or scores based on the inputs. With that being said, training data for a predictive model machine learning model may be known diversity data correlated to estimated diversity data and/or scores. In some instances, a computing device 104 may not have complete population data so data may need to be extrapolated and one way to do that is by a predictive model machine learning model. Known diversity data used to train a predictive model machine learning model may include geographical location, distances from a facility, demographics, or any combination thereof. By using known diversity data of a specific, an extrapolation of the known diversity data may require less computing power 104 as a predictive model may be easily trained and used. It should be noted that a graphical user interface (GUI) may be used for inputting values and also displaying outputs of any machine learning model described herein.

In another embodiment, and still referring to FIG. 1, calculating the diversity score 148 may include using a Simpson's Diversity Index, D, where Simpson's Diversity Index may express the diversity of a single attribute within a given population by representing the relative proportion of categories present, using the following equation:

$$D=1-\Sigma p_i^2$$

Where $p_i$ represents the proportion of individuals in ith category. In an embodiment, and without limitation, D may be interpreted as the probability that any two individuals, from a given population, drawn at random will be from a different category within a specific diversity attribute. In another embodiment, and without limitation, D, within a given diversity attribute, may be maximized with increasingly equal representation among many categories within a given diversity attribute.

In an embodiment, and still referring to FIG. 1, calculating diversity score 148 may include using a Shannon's Diversity Index, H, where Shannon's Diversity Index may express the diversity of a single attribute within a given population by representing the number of different categories present, using the following equation:

$$H = -\sum_{i=1}^{s} p_i \ln p_i$$

Where $p_i$ represents the proportion of individuals in ith category. H is interpreted as the uncertainty of the identity, in regard to diversity, of any given individual within a population of interest. Derived from information theory, H is maximized with increasingly more categories within a given diversity attribute and with increasingly equal representation of each category within the diversity attribute of interest. The theoretical maximum possible H for a given diversity attribute increases as the number of categories within that diversity attribute increases. Shannon's diversity index is equally sensitive to rare and abundant species.

In an embodiment, and still referring to FIG. 1, calculating diversity scorer 148 may include using a Multidimensional Information Diversity Index, M, where M may capture multidimensional diversity across several variables with multiple categories. In some instances, multiple categories may not be evenly represented. In addition, M may account for an interdependence effect between dimensions of diversity and subsequently correct for an associated reduction in diversity.

In an embodiment, and still referring to FIG. 1, the contribution, or weight, of each diversity variable to the overall diversity of an individual or cohort of interest may be captured by using a multiple linear regression computational modeling derived from a Composite Diversity Index. In one embodiment, applicant diversity score 148 ($A_{DS}$) may be represented by the following formula:

$$A_{DS}=k\times(B_{W_2}-B_{W_1})$$

Where k represents the statistical weight of diversity, representative of its relationship with clinical performance. $B_{w1}$ represents the composite diversity index of cohort of interest without applicant of interest included, and $B_{w2}$ represents the composite index of cohort of interest with applicant of interest included. Additionally or alternatively, the contribution, or weight, of each diversity variable to the overall diversity of an individual or cohort of interest may be captured by using one or more machine-learning processes and/or models. Machine-learning processes and/or models may include without limitation non-linear regression computational models. For example, but without limitation, one or more non-linear regression computational models may include polynomial regressions, exponential functions, logarithmic functions, trigonometric functions, power functions, Gaussian functions, Lorentz distributions, and the like thereof. Machine learning process and/or model may receive training data to train the machine learning process and/or model. For example, machine learning process and/or model may receive an input of one or more diversity variables, correlated with a particular contribution or weight, into the machine learning process and/or model as a training example. Machine learning process and/or model may receive multiple training examples (i.e., training data). That is, machine learning process and/or model may receive training data that trains the machine learning process and/or model to receive diversity variables and output a correlated contribution or weight.

Alternatively, or additionally, and still referring to FIG. 1. In one embodiment, computing device 104 may be configured to utilize machine learning processes to calculate the diversity score 148. In one embodiment, calculating the diversity score 148 may further include utilizing an artificial neural network. In one embodiment, calculating the diversity score 148 may include utilizing inherent and acquired attributes of an applicant.

In an embodiment, and still referring to FIG. 1, representative score 144 may include a competency score 152 as a function of the applicant profile 136. A "competency score" is a measurable value of an applicant's potential success with a given area of interest. That is, an "applicant's potential success" is a measure, metric, or any quantitative value representing a probability of an applicant succeeding within a given area of interest by predicting the applicant's performance in view of the measure and/or metric. A competency score 152 may represent an applicant's potential as a function of historical successes and failures within a context of the applicant's opportunities and resources. In one embodiment, identifying the applicant's competency score ($A_{CS}$) may include the following formula:

$$A_{CS} = \Sigma[k \times CS_i]$$

Where k represents the statistical weight of the $i^{th}$ competency, which is representative of its relationship with performance evaluations, and $CS_i$ represents the Applicant Competency Score in the $i^{th}$ competency. In one embodiment, and without limitation, identifying the competency score 152 may further include utilizing a Wilcoxon Rank Sum test to compare competency "performance" between two groups. Additionally or alternatively, identifying the competency score 152 may further include utilizing a plurality of statistical analysis such as but not limited to an Independent Group t-test, Paired t-test, ANOVA, string distance measurement such as, but not limited to, determining a Levenshtein distance, Srensen-Dice coefficient, block distance, Hamming distance, Jaro-Winkler distance, simple matching coefficient, Jaccard similarity, Tversky index, overlap coefficient, variational distance, Hellinger distance, information radius, skew distance, confusion probability, Tau metric, Fellegi and Sunters metric, maximal match, grammar-based distance, TFIDF distance, Kendell and Pearson correlation coefficients, and the like thereof. "Performance" may be determined by a computational model that utilizes both qualitative and quantitative data to determine an applicant's performance per competency. In one embodiment, determining an applicant's performance per competency may include reviewing an applicant's application in its entirety to break it into its individual components, followed by associating individual components to their contextual and cultural definitions in order to determine their "meaning". Determining an applicant's performance may further include associating qualitative and quantitative data with specific competencies based on their meanings and context within the application to create a single "performance" score per competency.

Alternatively, or additionally, and still referring to FIG. 1, identifying the competency score 152 may include utilizing a machine learning process. In one embodiment, identifying the competency score 152 may further include utilizing an artificial neural network. In one embodiment, identifying the competency score 152 may further utilize sensitivity analysis to check variable pre and post weighting to check for accuracy. In one embodiment, identifying the competency score 152 may include utilizing mixed linear and/or non-linear regression modeling.

Continuing to refer to FIG. 1, computing device 104 is further configured to generate a ranking score 156 as a function of representative score 144, wherein representative score 144 may include one or more diversity scores and/or competency scores. generating the applicant's ranking score ($A_{RS}$) may include utilizing the following formula:

$$A_{RS} = \frac{A_{CS} + A_{DS}}{M_{CS} + M_{DS}}$$

Where $M_{CS}$ is representative of the maximum possible competency score 152, and $M_{DS}$ is representative of the maximum possible diversity score 148.

Figure 2:
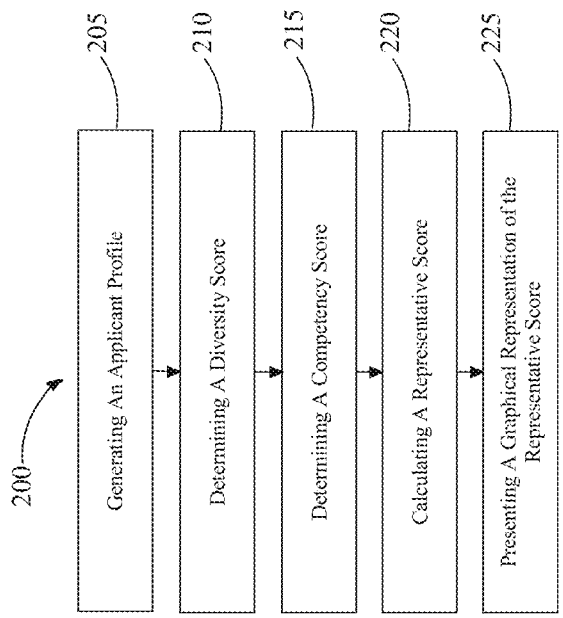
FIG. 2 is a flow diagram illustrating a method of diverse candidate selection.

Now referring to FIG. 2, an exemplary embodiment of a method 200 is shown. At step 205, method 200 includes generating an applicant profile 136. In some instances, generating an applicant profile 136 may include receiving a data input 108 into a machine learning process 140 as described herein. The data input 108 may include an expert dataset, such as one created by an education association, which is received through an API call. In another nonlimiting example, data input 108 may include an applicant's application to the residency program. In a nonlimiting example, the data input 108 may include a recommendation letter for the applicant sent to the residency program. In some instances, data input 108 may include an applicant identifier that may be an applicant's name. In yet another non-limiting example, data input 108 may include an applicant's resume, curriculum Vitale, and/or any job history information and/or volunteer experience. In another instance, applicant identifier may be an applicant's id used throughout a plurality of data. In another instance, an applicant's id and name may be correlated and an identifier may be created as a function of both, this may be useful as the data input 108 may include data that refers to the candidate by name and other data may only include an id for the candidate. In yet another instance, applicant identifier may be encrypted and/or deidentified whereby the applicant may be unable to be identified. In such an instance, data may be de-identified using a separate protocol to preserve applicant privacy and/or identity. In yet instance, applicant identifier may not exist, such as when data may be utilized that is open source and/or publicly available in the public domain and may already be de-identified.

Still referring to step 205 of method 200, generating an applicant profile 136 may include generating a textual query and applying the textual query to the data input 108. A "textual query" is a query for information associated with the diversity of an applicant. A textual query may cause a computing device and/or module to parse data input 108 for information associated with the diversity of an applicant using character strings. That is, a textual query may parse data input 108 for character strings including but not limited to "race", "gender", "sexual orientation", or the like. In some instances, a textual query may parse data input for character strings including but not limited to "work", "research", "languages spoken", "salary", "wages", "education", "certifications", "life skills", "hobbies", or the like. In a further nonlimiting example, a query may be for "applicant's past job", where the textual output may be words throughout the data input 108 that references any word in the query "applicant's past job." As another further nonlimiting example, some documents included in the data input may have words that show positive traits related to a candidate's past job, such as the applicant's personal statement, but other documents in the data input 108 may have negative traits related to that candidate's past job, such as a performance review. This information may be associated with the diversity of an applicant and may be used to determine a diversity score 148. Moreover, a textual output may be extracted from the result of a textual query and be used to produce applicant profile 136. It should be noted that applying a textual query to data input 108 may include matching, directly or indirectly, keyword strings. Additionally or alternatively, applying a textual query to data input 108 may include a vector comparison to keywords or generating one or more synonyms for keyword matching, As described herein, a language processing module may be used to implement a textual query to data input 108.

Still referring to FIG. 2, at step 210, method 200 may include determining a diversity score for an applicant. In some instances, determining a diversity score for an applicant may include parsing applicant profile 136 for diversity data associated with predetermined diversity indices. "Diversity data" is a textual output from a query for diversity attributes including but not limited to "race", "gender", "sexual orientation", or the like. Additionally, "predetermined diversity indices" are numerical values representative of diversity data. That is, predetermined diversity indices may be "race", "gender", "sexual orientation", or the like, but converted into numerical values using indexing methods as described herein. In addition, determining a diversity score may include calculating, based at least on predetermined diversity indices, the diversity score. For example, each numerical diversity value associated with each predetermined diversity index may be represented by a vector of any length less than or equal to one. Further, each predetermined diversity index may be associated with an axis, and all the predetermined diversity indices axes are orthogonal. The vector representation of the numerical diversity values will be discussed in further detail below. In a nonlimiting example, the diversity score 148 may be calculated by gathering attributes related to an applicant's diversity, which may be an inherent attribute, wherein an inherent attribute may include but is not limited to attributes an individual is born with including gender, race, ethnicity, nationality, where the applicant is from, and the like thereof and/or an acquired attribute, those gained through life experience, such as where the applicant went to school, from the applicant's profile and deriving weights for each attribute. In a further nonlimiting example, the applicant's diversity attributes may be further divided into categories, such as one category for educational background and another for personal background.

Still referring to FIG. 2, at step 215, method 200 may include determining a competency score for an applicant. While the output is a different score, the process for determining a competency score for an applicant follows the same series of steps as mentioned above with reference to step 210 of method 200. However, it should be noted that the process for determining a competency score differs in that applicant profile 136 may be parsed for competency data associated with predetermined competency indices. That is, competency data is a textual output from a query for competency attributes including but not limited to "previous job experiences", "education history", "volunteering", or the like, which is then extracted converted into predetermined competency indices. Further, "predetermined competency indices" are numerical values representative of competency data. A process of converting competency data into predetermine diversity indices may be the same or similar to that of converting diversity data as described above. In a nonlimiting example, attributes related to competency may be further parsed by a machine learning process as to extrapolate a performance per competency from qualitative and quantitative data. As a further nonlimiting example, an attribute related to competency may include a performance review from a past experience, which may include a grade, and statements made about the applicant's past experience, such statements that include words such as "caring" or "attentive", the attribute may then be parsed through a machine learning process 140 and a competency score 152 may be calculated. Moreover, predetermined diversity indices may be used to calculate a competency score 152 for an applicant. It should be noted that step 201 and step 215 may be interchangeable. That is, diversity score 148 may be determined first while competency score 152 is determined second, and vice-versa. Additionally, diversity score 148 and competency score 152 may be determined simultaneously (i.e., in parallel). As such, steps 210 and 215 may be combined.

Still referring to FIG. 2, at step 220, method 200 may include calculating a representative score. Calculating a representative score for an applicant based at least on the applicant's diversity score and the applicant's competency score. That is, a representative score may be calculated using arithmetic operations using numerical values of a diversity score and a competency score. In addition, a representative score may be calculated using vector addition. As noted above, a diversity score and a competency score may be represented as vectors, and those vectors may be added, subtracted, multiplied, or divided. For example, a diversity score vector and a competency score vector may be multiplied using a dot product or a cross product. As commonly known in the field of mathematics, a "dot product" is the product of magnitudes of vectors and a cosine of the angle between them. Further, a "cross product" is a product of magnitudes of vectors and a sine angle between them. Moreover, the final product of a dot product is a scalar quantity, while the final product of a cross product is a vector quantity.

Still referring to FIG. 2, at step 225, method 200 may include presenting a graphical representation of the representative score. In some instances, a graphical representation of the representative score may include but is not limited to a histogram, a dot plot, a pie graph, a bar graph, a table, or the like. For example, a graphical representation may illustrate a comparative analysis of a representative score versus scores in an applicant pool or current attendees of a residency program or medical school. That is, a graphical representation may show, visually, in an easy to analyze manner, how an applicant compares to an applicant pool or current attendees. This allows for admissions to easily compare applicants to one another and current attendees with having to parse through a series of documents to get a comprehensive perspective of an applicant. Thus, streamlining the admission process, for both an applicant and respective admission offices.

With continued reference to FIG. 2, a "vector" as defined in this disclosure is a data structure that represents one or more quantitative values and/or measures diversity scores and competency scores. A vector may be represented as an n-tuple of values, where n is one or more values, as described in further detail below; a vector may alternatively or additionally be represented as an element of a vector space, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent, for instance as measured using cosine similarity as computed using a dot product of two vectors; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\Sigma_{i=0}^{n} a_i^2}$, where $a_i$ is attribute number i of the vector. Scaling and/or normalization may function to make vector comparison independent of absolute quantities of attributes, while preserving any dependency on similarity of attributes.

As briefly discussed above, a diversity score and a competency score may be represented by a vector. respectively. In some embodiments, a diversity score and a competency score may be represented by vectors, respectively. For example, a diversity score vector may have numerical values corresponding to various diversity indices. A competency score vector may have numerical values corresponding to a various competency indices. By using vector multiplication, more specifically cross product multiplication, an area can be defined by a cross product of a diversity score vector and a competency score vector. In some instances, the area may be used to represent a representative score. It should be noted that to perform a cross product, vectors must be the same size. For example, a diversity score must have the same number of indices as a competency score such that when they are both converted into vectors, a cross product operation may be performed. In some embodiments, filler indices may be utilized. For example, if a number of indices do not match, "0" valued inputs may be added to the score (e.g., diversity score, competency score) that has the lesser number of indices. This may be done such that respective score vectors may be built with the same number of inputs and a cross product may still be calculated.

Figure 3:
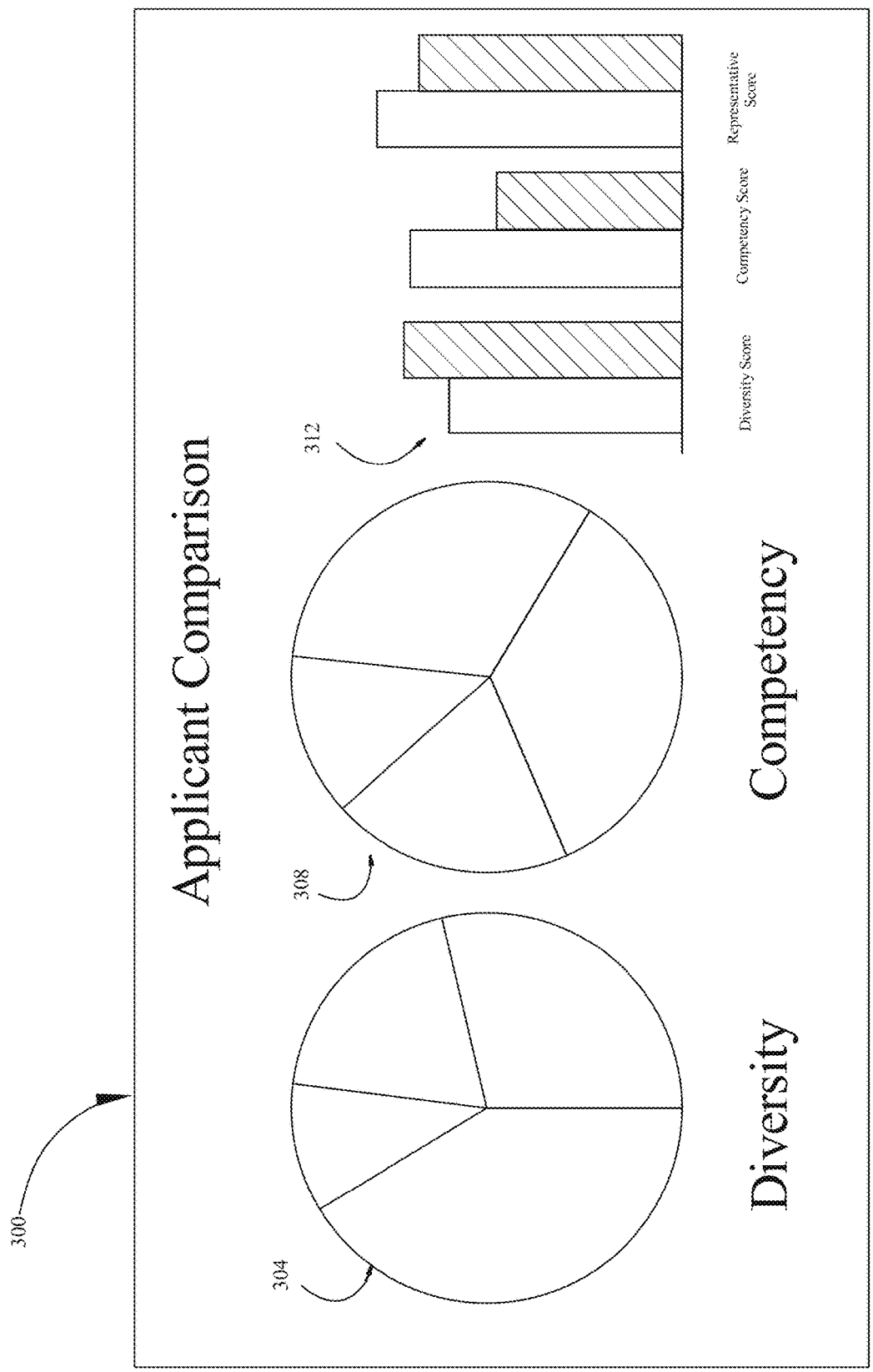
FIG. 3 is an illustrative embodiment of a visual interface displaying applicant data.

Referring now to FIG. 3, exemplary embodiment of a visual interface is illustrated. Computing device 104 is configured to provide a visual interface 300. Visual interface 300 may be displayed using include any device suitable for use as computing device 104 or user display, including without limitation an end-user device such as a desktop computer, work terminal, laptop computer, netbook, mobile device such as a smartphone or tablet, or the like. A "visual interface," as used in this disclosure, graphical user interface (GUI) that permits user to manipulate, move, edit, connect together, and/or otherwise interact with a diversity graphic 304, a competency graphic 308, a comparative graphic 312 and/or combinations thereof. Visual interface 600 may include a window in which diversity graphic 304, competency graphic 308, comparative graphic 312 and/or combinations thereof, to be used may be displayed. Visual interface 600 may include one or more graphical locator and/or cursor facilities allowing a user to interact with a diversity graphic 304, competency graphic 308, a comparative graphic 312 and/or combinations thereof, for instance using a touchscreen, touchpad, mouse, keyboard, and/or other manual data entry device. Visual interface 600 may include one or more menus and/or panels permitting selection of tools, options, for diversity graphic 304, competency graphic 308, comparative graphic 312 and/or combinations thereof to be displayed and/or used, elements of data, functions, or other aspects of a diversity graphic 304, competency graphic 308, a comparative graphic 312 to be edited, added, and/or manipulated, options for importation of and/or linking to application programmer interfaces (APIs), exterior services, databases, machine-learning models, classifiers, and/or algorithms, or the like. Persons skilled in the art, upon reviewing the entirety of this disclosure, will be aware of various ways in which a visual interface 300 and/or elements thereof may be implemented and/or used as described in this disclosure.

Still referring to FIG. 3, comparative graphic 312 may include a comparative graph and/or chart that compares an applicant to an applicant pool. In some embodiments, comparative graphic 312 may compare applicant to a current representative score of attending medical students or residency program participants. Comparative graphic 312 may compare applicant's diversity score, competency score, representative score, and/or any combination thereof in efforts to streamline admissions processes. Further, applicant's diversity score, competency score, representative score, and/or any combination thereof may be compared to an applicant pool, current medical students, current program participants, and/or any combination thereof.

Continuing to refer to FIG. 3, as illustrated in comparative graphic 312, shaded columns may represent an applicant pool, current medical students, current program participants, and/or any combination thereof. The hollow columns may represent applicants scores. As such, each column may be interactive, such that a pop-up may be displayed with relevant information regarding the data used to calculate each score. For example, hovering over applicant's "Diversity Score" column of comparative graphic 312 may prompt a pop-up window with numerical values associated with the applicant's diversity score. Advantageously, an admissions officer may be provided with visual interface 300 when clicking on a particular applicant such that information associated the particular applicant is readily available and compiled into a single place to save navigation and computing time.

Figure 4:
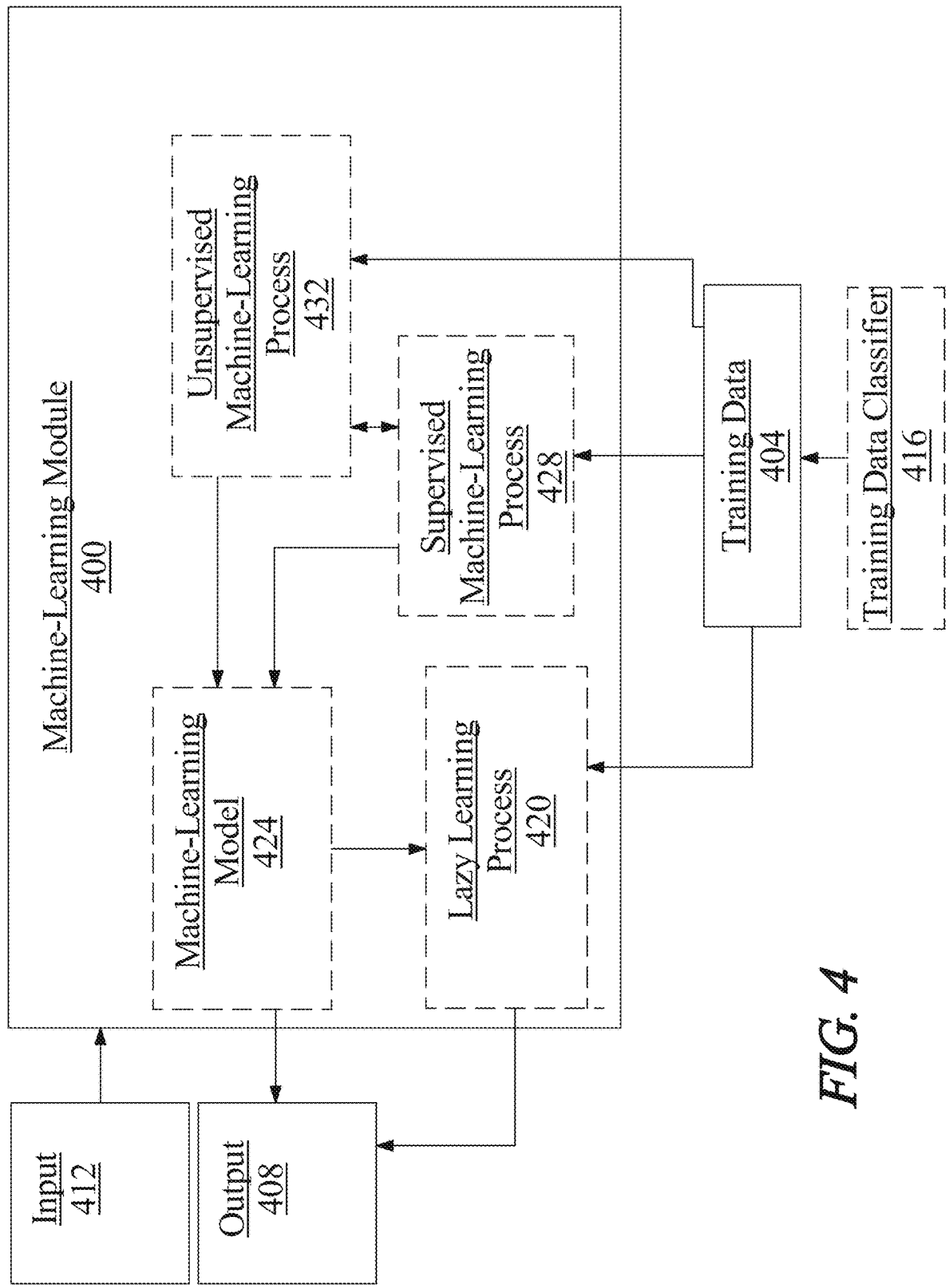
FIG. 4 is an exemplary embodiment of a machine learning module.

Referring now to FIG. 4, an exemplary embodiment of a machine-learning module 400 that may perform one or more machine-learning processes as described in this disclosure is illustrated. Machine-learning module may perform determinations, classification, and/or analysis steps, methods, processes, or the like as described in this disclosure using machine learning processes 140. A "machine learning process," as used in this disclosure, is a process that automatedly uses training data 404 to generate an algorithm that will be performed by a computing device/module to produce outputs 408 given data provided as inputs 412; this is in contrast to a non-machine learning software program where the commands to be executed are determined in advance by a user and written in a programming language.

Still referring to FIG. 4, "training data," as used herein, is data containing correlations that a machine-learning process may use to model relationships between two or more categories of data elements. For instance, and without limitation, training data 404 may include a plurality of data entries, each entry representing a set of data elements that were recorded, received, and/or generated together; data elements may be correlated by shared existence in a given data entry, by proximity in a given data entry, or the like. Multiple data entries in training data 404 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 404 according to various correlations; correlations may indicate causative and/or predictive links between categories of data elements, which may be modeled as relationships such as mathematical relationships by machine-learning processes as described in further detail below. Training data 404 may be formatted and/or organized by categories of data elements, for instance by associating data elements with one or more descriptors corresponding to categories of data elements. As a non-limiting example, training data 404 may include data entered in standardized forms by persons or processes, such that entry of a given data element in a given field in a form may be mapped to one or more descriptors of categories. Elements in training data 404 may be linked to descriptors of categories by tags, tokens, or other data elements; for instance, and without limitation, training data 404 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 4, training data 404/ may include one or more elements that are not categorized; that is, training data 404 may not be formatted or contain descriptors for some elements of data. Machine-learning algorithms and/or other processes may sort training data 404 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 404 to be made applicable for two or more distinct machine-learning algorithms as described in further detail below. Training data 404 used by machine-learning module 400 may correlate any input data as described in this disclosure to any output data as described in this disclosure. As a non-limiting illustrative example competency scores and/or diversity scores may be inputs, wherein an output may be a ranking score.

Further referring to FIG. 4, training data may be filtered, sorted, and/or selected using one or more supervised and/or unsupervised machine-learning processes and/or models as described in further detail below; such models may include without limitation a training data classifier 416. Training data classifier 416 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 400 may generate a classifier using a classification algorithm, defined as a process whereby a computing device and/or any module and/or component operating thereon derives a classifier from training data 404. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 416 may classify elements of training data to sub-categories of diversity scores, competency scores, representative scores, and the like thereof.

Still referring to FIG. 4, machine-learning module 400 may be configured to perform a lazy-learning process 420 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 404. Heuristic may include selecting some number of highest-ranking associations and/or training data 404 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 4, machine-learning processes as described in this disclosure may be used to generate machine-learning models 424. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 424 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 424 may be generated by creating an artificial neural network, such as a convolutional neural network comprising an input layer of nodes, one or more intermediate layers, and an output layer of nodes. Connections between nodes may be created via the process of "training" the network, in which elements from a training data 404 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 4, machine-learning algorithms may include at least a supervised machine-learning process 428. At least a supervised machine-learning process 428, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include diversity scores and/or competency scores as described above as inputs, ranking scores as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 404. Persons skilled in the art, upon reviewing the entirety of this disclosure, will be aware of various possible variations of at least a supervised machine-learning process 428 that may be used to determine relation between inputs and outputs. Supervised machine-learning processes may include classification algorithms as defined above.

Further referring to FIG. 4, machine learning processes 140 may include at least an unsupervised machine-learning processes 432. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 4, machine-learning module 400 may be designed and configured to create a machine-learning model 424 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure. Additionally or alternatively, machine-learning module 400 may be designed and configured to create a machine-learning model 424 using techniques for development of non-linear regression models. Non-linear regression models may include one or more non-linear regression computational models such as but not limited to polynomial regressions, exponential functions, logarithmic functions, trigonometric functions, power functions, Gaussian functions, Lorentz distributions, and the like thereof.

Continuing to refer to FIG. 4, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 5:
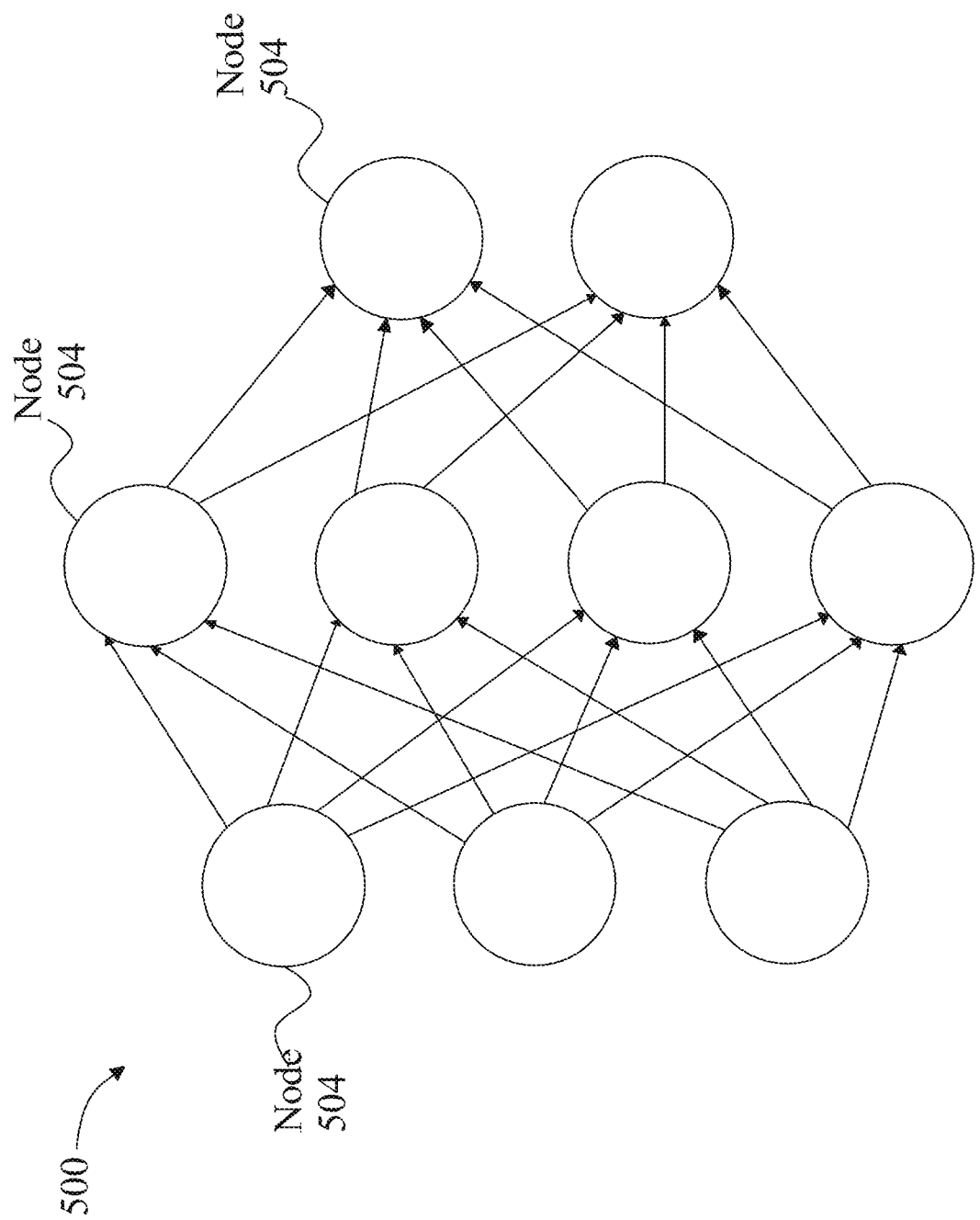
FIG. 5 is an illustrative embodiment of a neural network.

Referring now to FIG. 5, an exemplary embodiment of neural network 500 is illustrated. A neural network also known as an artificial neural network, is a network of "nodes," or data structures having one or more inputs, one or more outputs, and a function determining outputs based on inputs. Such nodes 504 may be organized in a network, such as without limitation a convolutional neural network, including an input layer of nodes 504, one or more intermediate layers, and an output layer of nodes 504. Connections between nodes 504 may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Figure 6:
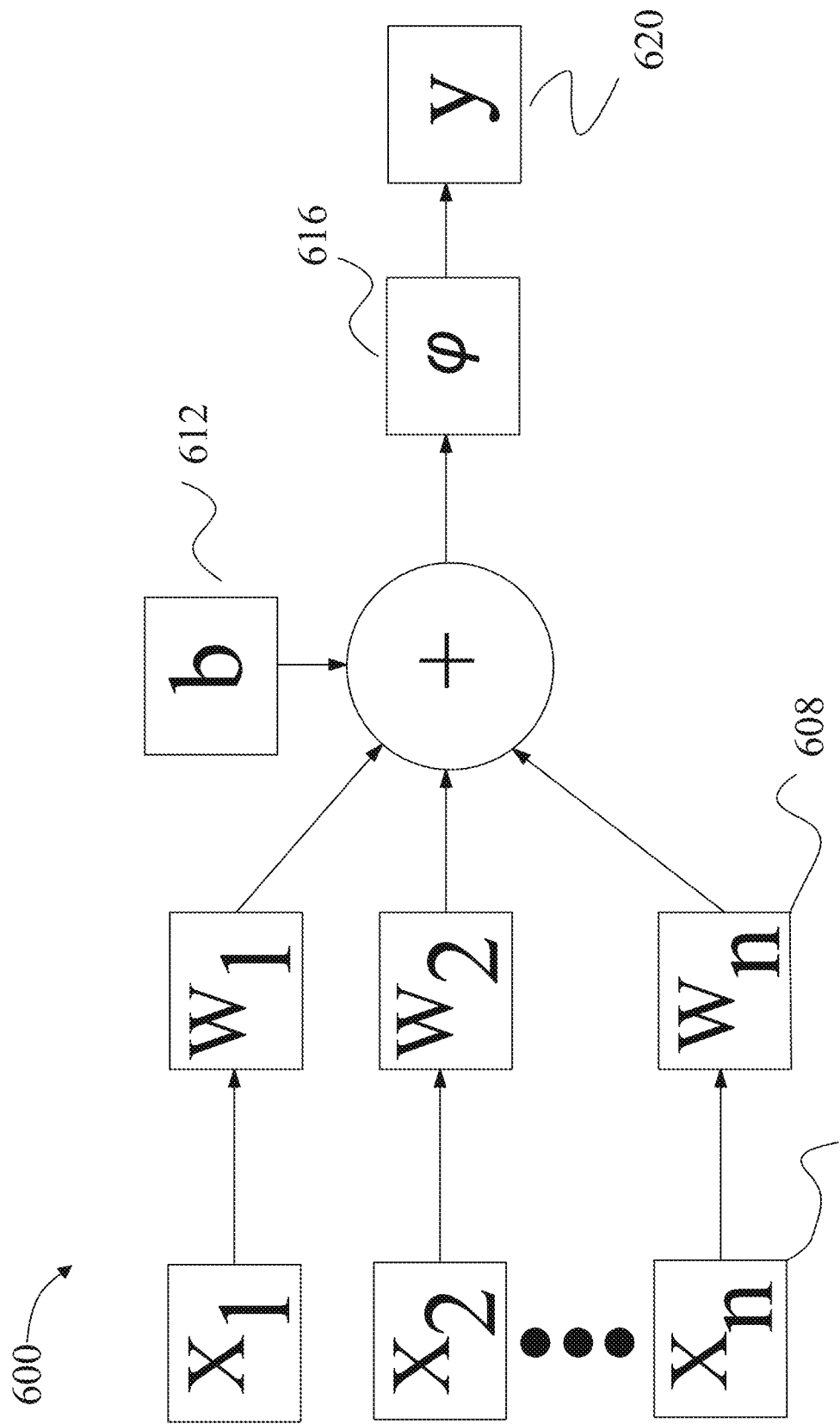
FIG. 6 is an exemplary embodiment of a neural network node.

Referring now to FIG. 6, an exemplary embodiment of a node 600 of a neural network 500 is illustrated. A node may include, without limitation a plurality of inputs $x_n$ 604 that may receive numerical values from inputs to a neural network containing the node and/or from other nodes. Node may perform a weighted sum of inputs using weights $w_n$ 608 that are multiplied by respective inputs $x_n$ 604. Additionally or alternatively, a bias b 612 may be added to the weighted sum of the inputs such that an offset is added to each unit in the neural network layer that is independent of the input to the layer. The weighted sum may then be input into a function φ 616, which may generate one or more outputs y 620. Weight $w_n$ 608 applied to an input $x_n$ 604 may indicate whether the input is "excitatory," indicating that it has strong influence on the one or more outputs y, for instance by the corresponding weight having a large numerical value, and/or a "inhibitory," indicating it has a weak effect influence on the one more inputs y 620, for instance by the corresponding weight having a small numerical value. The values of weights $w_n$ 608 may be determined by training a neural network using training data, which may be performed using any suitable process as described above. In an embodiment, and without limitation, a neural network may receive semantic units as inputs and output vectors representing such semantic units according to weights $w_n$ that are derived using machine-learning processes as described in this disclosure.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
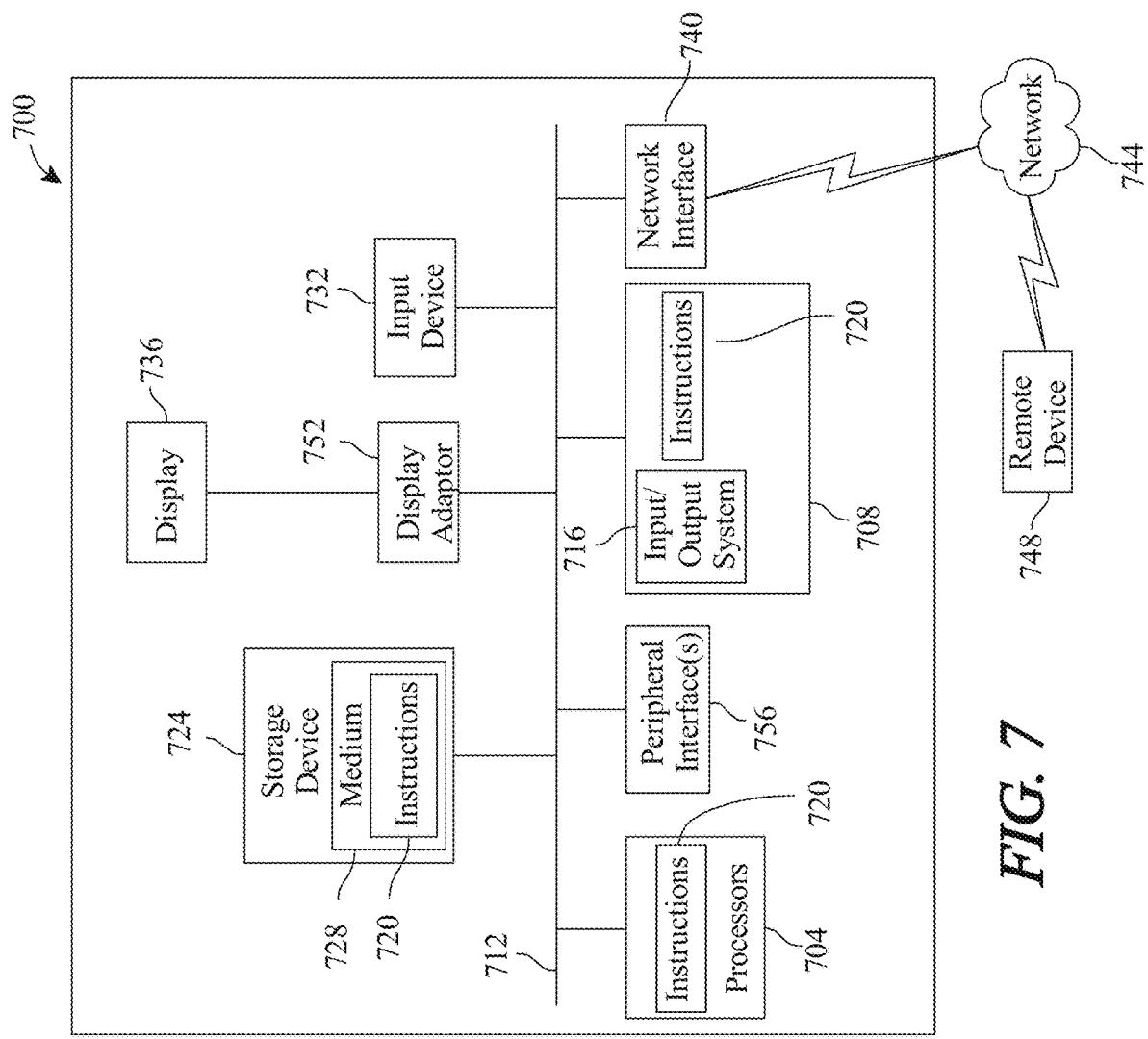
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIRE-WIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A method for holistic medical student and medical residency matching, comprising:
   generating, by a processor, an applicant profile, wherein generating the applicant profile comprises:
   receiving applicant data;
   generating a textual query for the applicant data;
   applying the textual query to the applicant data,
   extracting a textual output based at least on the textual query; and
   producing the applicant profile based at least on the textual output of the textual query; and
   determining, by the processor, a diversity score, wherein determining the diversity score comprises:
   parsing the applicant profile for diversity data associated with predetermined diversity indices;
   extracting the diversity data associated with the predetermined diversity indices;

converting the diversity data associated with the predetermined diversity indices into numerical diversity values; and calculating, based at least on the numerical diversity values, the diversity score; and determining, by the processor, a competency score, wherein determining the competency score comprises:

parsing the applicant profile for competency data associated with predetermined competency indices;

extracting the competency data associated with the predetermined competency indices;

converting the competency data associated with the predetermined competency indices into numerical competency values; and calculating, based at least on the numerical competency values, the competency score; and calculating, by the processor, a representative score for an applicant based at least on the diversity score and the competency score, wherein the calculation comprises:

training a machine learning model using training data, wherein the machine learning model comprises at least a neural network, wherein the training data contains a plurality of data entries containing a plurality of applicant diversity scores and applicant competency scores as inputs correlated to a plurality of representative scores as outputs; and calculating the representative score for the applicant as a function of the applicant diversity score and the applicant competency score using a trained machine learning model, wherein calculating the representative score comprises:

calculating a cross product of a diversity score vector and a competency score vector, wherein:

the diversity score vector has a first number of indices and the competency score vector has a second number of indices;

the first number of indices and the second number of indices are different; and the cross product is calculated by adding a number of zero index values equal to the difference between the first number of indices and the second number of indices to:

the diversity score vector if the first number of indices is less than the second number of indices, or the competency score vector if the first number of indices is greater than the second number of indices; and outputting the representative score in the form of a vector; and presenting, on a graphical user interface (GUI), a graphical representation of the representative score.

2. The method of claim 1, wherein calculating the representative score comprises utilizing a Sullivan's Composite Diversity Index.

3. The method of claim 1, wherein calculating the representative score comprises utilizing a Simpson's Diversity Index.

4. The method of claim 1, wherein determining the diversity score comprises utilizing statistical weighting of the predetermined diversity indices.

5. The method of claim 4, wherein the statistical weighting of the predetermined diversity indices includes a Wilcoxon rank sum test.

6. The method of claim 4, wherein the statistical weighting of the predetermined diversity indices includes a consensus method to assign the weight of each of the predetermined diversity indices.

7. The method of claim 1, wherein an applicant ranking score is a function of a maximum possible competency score.

8. The method of claim 1, wherein an applicant ranking score is a function of a maximum possible diversity score.

9. A system for holistically ranking medical student and medical residency matching, wherein the system comprising:

at least a processor; and a memory communicatively connected to the at least a processor, the memory containing instructions configuring the at least a processor to:

generate an applicant profile, wherein generating the applicant profile causes the processor to comprises a language processing module:

receive applicant data, wherein the applicant data is in a textual format;

generate a textual query for the applicant data;

apply the textual query to the applicant data;

extract a textual output based at least on the textual query; and produce the applicant profile based at least on the textual output of the textual query; and determine a diversity score, wherein determining the diversity score causes the processor to:

parse the applicant profile for diversity data associated with predetermined diversity indices;

convert the diversity data into the predetermined diversity indices; and calculate, based at least on the predetermined diversity indices, the diversity score; and determine a competency score, wherein determining the competency score causes the processor to:

parse the applicant profile for competency data associated with predetermined competency indices;

convert the competency data into the predetermined competency indices;

calculate, based at least on the predetermined competency indices, the competency score; and calculate a representative score for an applicant based at least on the diversity score and the competency score, wherein the calculation comprises:

training a machine learning model using training data, wherein the machine learning model comprises at least a neural network, wherein the training data contains a plurality of data entries containing a plurality of applicant diversity scores and competency scores as inputs correlated to a plurality of representative scores as outputs; and calculating the representative score for the applicant as a function of the diversity score and the competency score, wherein calculating the representative score comprises:

calculating a cross product of a diversity score vector and a competency score vector, wherein:

the diversity score vector has a first number of indices and the competency score vector has a second number of indices;

the first number of indices and the second number of indices are different; and the cross product is calculated by adding a number of zero index values equal to the difference between the first number of indices and the second number of indices to:
the diversity score vector if the first number of indices is less than the second number of indices, or
the competency score vector if the first number of indices is greater than the second number of indices; and
outputting the representative score in the form of a vector; and
present, on a graphical user interface (GUI), a graphical representation of the representative score.

10. The system of claim 9, wherein the processor utilizes Sullivan's Composite Diversity Index to calculate the representative score.

11. The system of claim 9, wherein the processor utilizes Simpson's Diversity Index to calculate the representative score.

12. The system of claim 9, wherein the diversity score comprises statistical weighting of the predetermined diversity indices.

13. The system of claim 12, wherein the statistical weighting of the predetermined diversity indices includes a Wilcoxon rank sum test.

14. The system of claim 12, wherein the statistical weighting of the predetermined diversity indices includes a consensus method to assign the weight of each of the predetermined diversity indices.

15. The system of claim 9, wherein an applicant ranking score is a function of a maximum possible competency score.

16. The system of claim 9, wherein an applicant ranking score is a function of a maximum possible diversity score.

* * * * *